United States Patent [19]

Ritter et al.

[11] Patent Number: 4,932,963
[45] Date of Patent: Jun. 12, 1990

[54] COMBINED SURGICAL NEEDLE-SUTURE DEVICE POSSESSING AN INTEGRATED SUTURE CUT-OFF FEATURE

[75] Inventors: Thomas A. Ritter, Sandy Hook; George R. Proto, West Haven; Edward C. White, Orange, all of Conn.

[73] Assignee: United States Surgical Corporation, Norwalk, Conn.

[21] Appl. No.: 317,948

[22] Filed: Mar. 2, 1989

[51] Int. Cl.$^5$ ............................................. A61B 17/06
[52] U.S. Cl. .................................... 606/224; 606/227
[58] Field of Search ............................. 128/339, 335.5; 606/224–227

[56] References Cited

U.S. PATENT DOCUMENTS

| | | | |
|---|---|---|---|
| 86,769 | 2/1969 | Marriott | 128/339 |
| 1,757,129 | 5/1930 | McClure | 128/339 |
| 2,910,983 | 11/1959 | Everett | 128/339 |
| 3,799,169 | 3/1974 | Beroff et al. | 128/339 |
| 3,910,282 | 10/1975 | Messer et al. | 128/339 |
| 3,926,194 | 12/1975 | Greenberg et al. | 128/339 |
| 3,943,933 | 3/1976 | Gertzman | 128/339 |
| 3,949,756 | 4/1976 | Ace | 128/339 |
| 4,072,041 | 2/1978 | Hoffman et al. | 128/339 |
| 4,799,483 | 1/1989 | Kraff | 128/339 |
| 4,805,292 | 2/1989 | Noguchi | 128/339 |

*Primary Examiner*—Edward M. Coven
*Assistant Examiner*—Gary Jackson
*Attorney, Agent, or Firm*—Peter G. Dilworth; Rocco S. Barrese; Thomas R. Bremer

[57] ABSTRACT

A combined surgical needle-suture device is disclosed in which the suture is received into a socket, or recess, formed within the blunt end of the needle, the entrance to the socket being defined by a circumferential sloping surface which terminates at its outer end in a circumferential cutting edge which provides quick and convenient suture cut-off capability when severing of the suture from the needle is desired.

7 Claims, 3 Drawing Sheets

COMBINED SURGICAL NEEDLE-SUTURE DEVICE POSSESSING AN INTEGRATED SUTURE CUT-OFF FEATURE

CROSS REFERENCE TO RELATED APPLICATION

This application relates by subject matter to commonly assigned, concurrently filed U.S. patent application entitled "Apparatus For Forming a Suture Cut-Off Feature In A Surgical Needle Possessing a Suture-Receiving Socket" [U.S. Ser. No. 317,949].

BACKGROUND OF THE INVENTION

This invention relates to a combined surgical needle-suture device possessing an integrated suture cut-off feature and to a method for separating the needle from its attached suture.

The prior art describes a variety of arrangements for securing a suture within an axial socket, or recess, provided at the blunt end of a surgical needle and for providing release, or separation, of the needle from the suture upon completion of suturing. Illustrative of such suture-surgical needle combinations are those described in U.S. Pat. Nos. 1,757,129; 3,799,169; 3,910,282; 3,926,194; 3,943,933; 3,949,756; 4,054,144; and, 4,072,041. Specific techniques provided in these prior disclosures for achieving separation of the suture from the needle include peeling the suture out of a channel formed in the rear of the needle as shown in U.S. Pat. No. 3,799,169 and tugging sharply at the needle within some predetermined range of "pull-out" force to effect separation of the needle and suture at the site of a weakened suture segment as shown in U.S. Pat. Nos. 3,926,194; 3,943,933; 3,949,756; 4,054,144; and, 4,072,041.

U.S Pat. No. 2,910,983 describes a surgical needle-suture combination in which the suture is held securely within a crimped socket possessing an outer sharp circumferential edge. The sole disclosed function of the sharp edge is to provide a flared entrance to the socket thus preventing damage to the suture. There is no suggestion in U.S. Pat. No. 2,910,983 of providing a sharp edge for the purpose of achieving suture cut-off.

U.S. Pat. No. 86,769 describes a needle-and-thread combination for sewing canvas in which a forward section of the needle possesses a cutting edge for cutting the attached thread when desired.

SUMMARY OF THE INVENTION

It is an object of the present invention to provide a surgical needle-suture combination possessing a suture release feature.

It is a particular object of the invention to provide a socketed surgical needle-suture combination which provides for separation of the suture from the needle by a quick, sharp lateral movement of the suture away from the needle.

It is a further particular object of the invention to provide a socketed surgical needle-suture combination in which separation of the suture from the needle at their junction is achieved by application of a cutting movement to the suture while the suture is held under tension upon any point along a circumferential cutting edge defined upon the socketed end of the needle.

In keeping with these and other objects of the invention, in a combined surgical needle-suture device which includes a surgical needle having a sharp end and a blunt end with a suture-receiving socket at said blunt end, a suture having one tip received within said socket and means for retaining the tip of the suture within the socket, an improvement is provided which comprises a circumferential sloping surface defining the entrance to the socket, said sloping surface terminating at one end in the socket and at the other end in a circumferential cutting edge, the slope of said surface being defined by an inclusive angle the minimum value of which is sufficient to preserve an amount of strength in the needle material associated with said cutting edge such that said needle material will resist being torn away during cutting of the suture against the circumferential cutting edge and the maximum value of which does not attain that at which the circumferential edge of the entrance of the socket is no longer effective as a cutting edge.

To effect separation of the needle from the suture, the suture is oriented relative to the needle such that the suture is made to bear against any location along the circumferential cutting edge of the needle socket entrance and, while the suture is held in tension against the cutting edge, an arc-like, or sweeping, movement of the suture against the cutting edge is employed to effect separation of the needle from the suture at their junction.

The suture cut-off feature of the combined surgical needle-suture device of this invention provides a quick, simple, convenient and effective means for achieving separation of the suture from the needle at any point along the circumferential cutting edge of the latter without the need for a separate cutting instrument. In general, the amount of force required to effect separation of the suture from the needle is significantly less than that required by known and conventional needle-suture combinations which require that some minimum "pull-out" force be applied to the suture against the needle or that some force which is sufficient to break a weakened suture segment be applied thereto.

Since the cutting movement required to effect separation of the suture from the needle of this invention is a deliberate one and is entirely distinct from any of the movements employed in suturing, there is no possibility that in the absence of a deliberate intention to sever the suture from the needle, there can be an accidental separation of the one from the other. Accordingly, unlike known and conventional surgical needle-suture combinations such as those referred to above, the combined surgical needle-suture device of this invention avoids any compromise in a firm attachment of the suture to the needle and permits the surgeon to sever the suture only by a deliberate, purposeful severing movement of the needle held in tension against the needle's circumferential cutting edge.

DESCRIPTION OF THE PREFERRED EMBODIMENTS

The apparatus of the present invention and its operation will be specifically described in connection with the manufacture of a preferred type of surgical needle, i.e., the socketed needle possessing a suture cut-off.

DESCRIPTION OF THE PREFERRED EMBODIMENTS

Figure 1A:
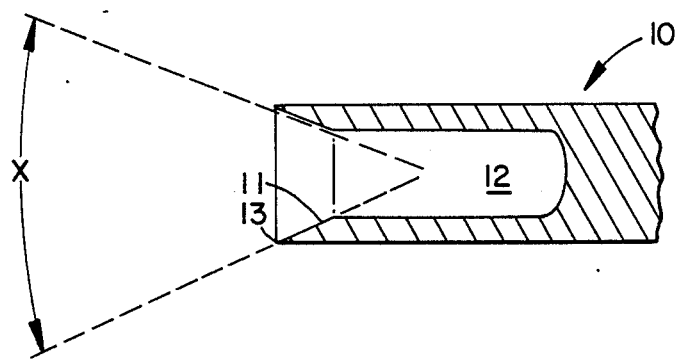
Figs. 1A and 1B are enlarged cross sectional views of the axial suture-receiving socket end of the surgical needle component of a surgical needle-suture combination in accordance with this invention showing the side profile of the socketed end of the needle before (FIG. 1A) and after (FIG. 1B) attachment of the tip of the suture to the needle.

As shown in FIG. 1A, the rear portion of surgical needle 10 possesses a sloping surface 11 defining the entrance to a concentrically positioned socket 12. Sloping surface 11 terminates in a circumferential cutting edge 13 which possesses an inclusive angle x formed at the junction of opposed sloped surfaces. The cutting edge can be smooth as shown or it can be notched or serrated to enhance its cutting action.

Figure 1B:
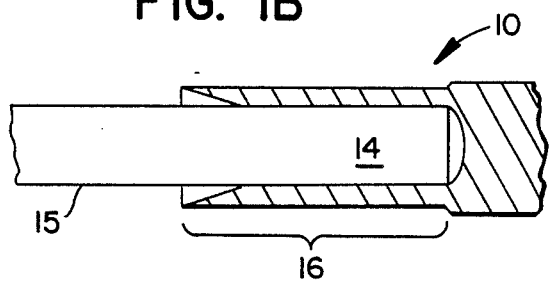

In FIG. 1B, tip 14 of suture 15 is shown occupying socket 12 of needle 10 and is held tightly within the socket by a crimping of needle section 16 about the tip of the suture. Crimping has no appreciable affect upon the value of inclusive angle X.

Aforesaid angle x which defines the slope of the socket entrance is critical to achieving effective suture cut-off. On the one hand, if the value for inclusive angle X is below a certain minimum (which depends upon the structural/mechanical properties of the material from which the needle is fabricated and can be readily determined in a given case by simple and routine testing), the slope of the socket entrance will be too steep for the needle material in the vicinity of the socket entrance to withstand the force of the tensioned cutting movement which is employed to sever the suture upon the circumferential cutting edge. If, on the other hand, the value for inclusive angle X exceeds a certain maximum (again, as in the case of the minimum value of X, a variable which depends some extent upon the nature of the material from which the needle is fabricated and is readily determined for a specific needle construction by simple, routine testing), the slope of the socket entrance will be too shallow to provide an effective cutting edge. For surgical needles manufactured from any of the stainless steels which are commonly used for the construction of such needles, the value of inclusive angle X is advantageously on the order of from about 90° to about 110° and preferably is from about 95° to about 105°.

In addition to the values, supra, for inclusive angle X, other suitable dimensions for various sizes of needle-suture devices in accordance with this invention are set forth in the following table.

TABLE

Needle Dimensions

| Suture Size Designation | Suture Diameter (mm) | Suture Diameter (inches) | Needle Diameter, inches | Socket Diameter, thousands of an inch (mils) | Socket Depth, inches |
| --- | --- | --- | --- | --- | --- |
| 6-0 | 0.070–0.099 | 0.0026–0.0039 | 0.013 | 6.4–7.0 | 0.030 |
| 5-0 | 0.10–0.149 | 0.0039–0.0059 | 0.015 | 8.8–9.6 | 0.035 |
| 4-0 | 0.15–0.199 | 0.0059–0.0078 | 0.017 0.022 | 10.2–11.0 | 0.042 |
| 3-0 | 0.20–0.249 | 0.0079–0.0098 | 0.024 0.039 | 12.5–13.5 | 0.050 |
| 2-0 | 0.030–0.399 | 0.0118–0.0133 | 0.026 0.039 0.050 | 15.2–16.2 | 0.057 |
| 1-0 | 0.35–0.399 | 0.0138–0.0157 | 0.039 0.044 0.050 | 18.2–19.2 | 0.060 |
| 1 | 0.40–0.499 | 0.0157–0.0196 | 0.039 0.044 0.050 | 21.2–22.2 | 0.070 |

Figure 2:
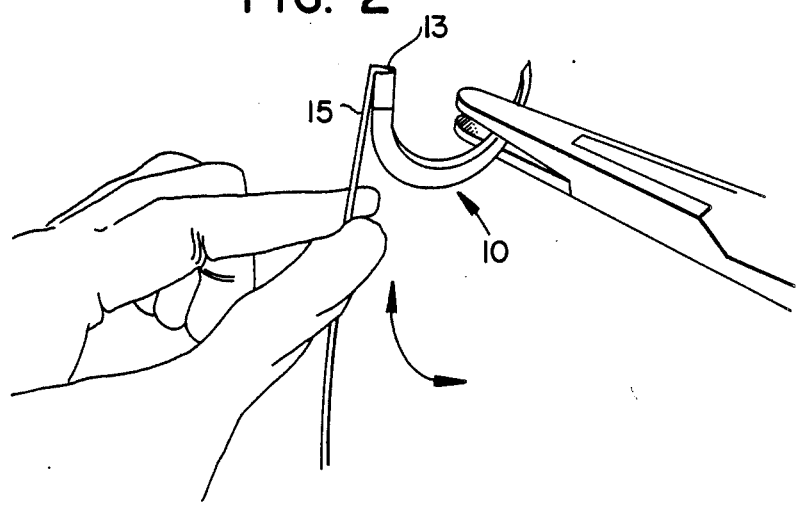
FIG. 2 illustrates the method of separating the suture from the needle in the surgical needle-suture combination of this invention.

While the surgical needle-suture combination herein is in use, suture 15 will ordinarily avoid contact with cutting edge 13 of socket entrance 11. Occasional, unintentional and non-tensioned contact of the suture with circumferential cutting edge 13 will not affect the integrity of the surgical needle-suture combination. However, upon completion of suturing when separation of the surgical needle from the suture is desired, a deliberate arc-like, or sweeping, movement applied to the tensioned suture generally in the direction indicated by the arrow in FIG. 2 will be sufficient to sever the suture against circumferential cutting edge 13. Depending upon the size of the suture, an amount of force on the order of from about 3 oz. to about 4.0 lb., and preferably from about 6 oz. to about 2.5 lb., and one or just a few back-and-forth sweeps of the suture against cutting edge will be effective to accomplish suture cut-off.

The surgical needle component herein can be fabricated from any suitable material, e.g., any of the stainless steels heretofore known or used for the construction of surgical needles. The needle can possess any appropriate shape, e.g., it can be straight or it can possess the largely curved configuration shown in FIG. 2.

Referring once again to Figs. 1A and 1B, circumferential sloping socket entrance 11, socket 12 and circumferential cutting edge 13 of needle 10 can be formed employing known or conventional machining techniques. However, it is particularly advantageous to form these elements employing the suture cut-off needle manufacturing apparatus of commonly assigned concurrently filed U.S. patent application Ser. No. 317,949, referred to above and illustrated in FIGS. 3A–D herein.

Figure 3A:
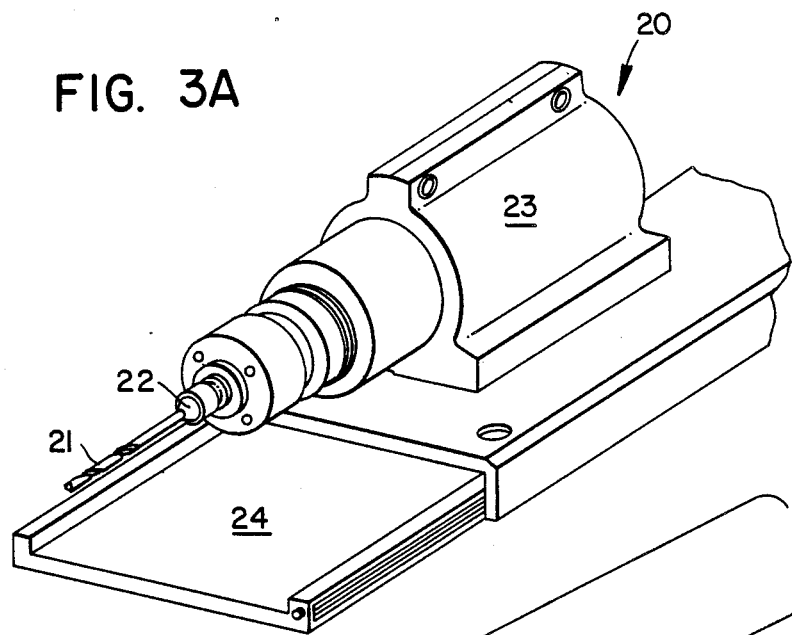
FIG. 3A is a perspective view of an axially movable cutting edge forming tool for use in an apparatus for forming the cutting edge in the surgical needle shown in FIGS. 1A–B and 2.

As shown in the apparatus of FIG. 3A, drilling unit 20 is provided as a fluted drill bit 21 held in spindle 22 of a high speed motor 23. Spindle 22 should be capable of holding drill 21 with considerable accuracy, e.g., with a maximum positional variation of no more than about 0.00015 inches. The drill together with its motor is supported upon a linear bearing member 24 which permits movement of drill 21 toward and away from the rear face of a socketed needle, e.g., with a straight line accuracy of at least 0.0005 in./in. of travel, as shown in FIG. 3D.

Figure 3B:
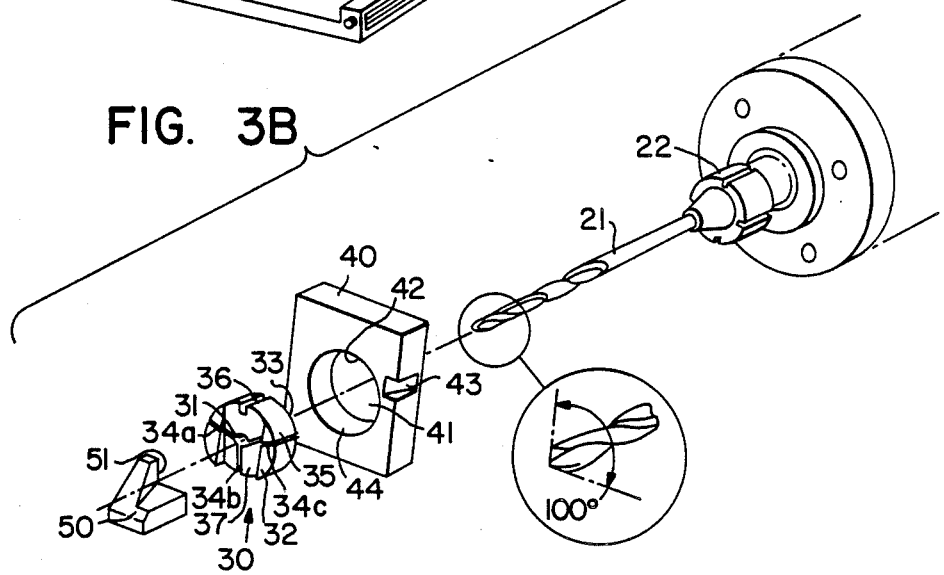
FIG. 3B is an exploded perspective view of the principal elements of the aforesaid cutting edge forming apparatus.
Figure 3C:
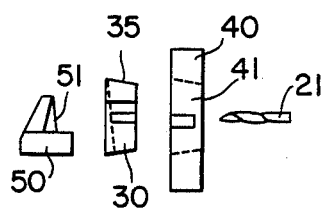
FIG. 3C is an exploded side elevational view of the locking ram, collet and collet holder elements of the apparatus of FIG. 3B; and, FIG. 3D is a perspective view of the assembled apparatus of FIG. 3B.
Figure 3D:
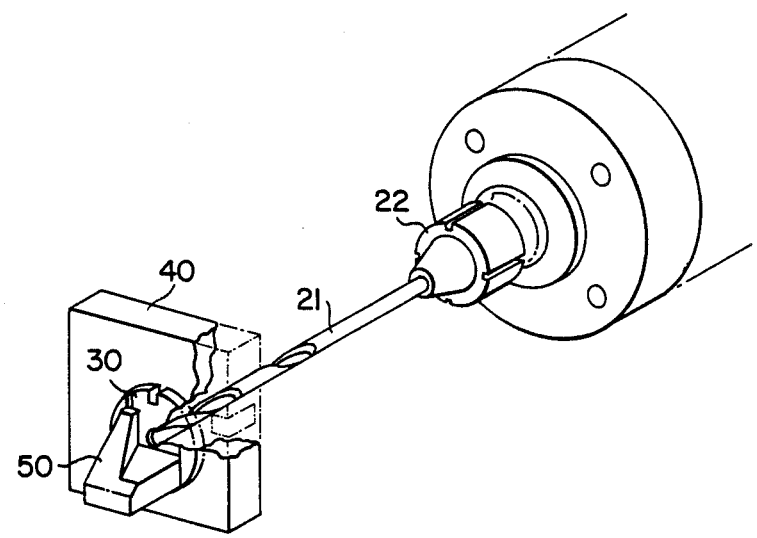

As shown in FIGS. 3B–D, needle receiving and holding collet 30 possesses a central bore 31 extending its full length for receiving the socketed end of a surgical needle. The collet possesses three slots 34a, 34b and 34c extending from its front face 33 to rear face 32 along conical shaped wall 35. These slots enable the collet to convert an axially directed force exerted against its rear face 32 to a circumferentially compressive force exerted against the blunt end of a needle present within bore 31 whereby the needle is held firmly and accurately in place within the collet for the subsequent circumferential suture-cutting edge-forming operation (as well as any optional socket forming operation). Collet holder 40 functions as a support frame for collet 30 and orients and guides the axial movement of the collet upon activation of locking ram 50. Opening 41 in collet holder 40 possesses a conical configuration providing an accurate mating support surface for collet 30 and permitting a limited degree of forward, axial movement of the collet therein when locking ram 50 is set in motion. Key 42 along the periphery of opening 41 of collet holder 40 cooperates with slot 36 in the collet to precisely orient the collet and make certain that the socketed end of the needle held within the collet is accurately positioned relative to drilling tool 21. Clearance slot 43 is provided on the collet holder in order to fully accommodate a curved needle during the machining thereof.

To accomplish locking of the needle within the collet and locking of the collet within its holder, a vertical movement of locking ram 50 against the upwardly sloping surface 37 of rear face 32 of collet 30 causes an axial forward movement of the collet within opening 41 of collet holder 40. Activation of locking ram 50 results in the application of an amount of force against collet 30 which is sufficient to slightly compress the sections of the collet as defined by slots 34a, 34b and 34c thereby securely locking the needle in place for drilling.

The geometries of those surfaces of collet 30, collet holder 40 and locking ram 50 which come into mutual contact during the locking step are important to achieving effective and accurate locking. Thus, the forward face 51 of locking ram 50 is so shaped as to present a downwardly sloping angle, in the embodiment shown, 5,° corresponding to the 5° angle of upwardly sloping surface 37 formed on the rear face 32 of collet 30. As the driving ram moves upwardly along a vertical axis which is perpendicular to the longitudinal axis of the collet, the resulting engagement of mating surfaces 51 and 37 forces collet 30 forward within the collet holder, the 9°30′ slope of collet wall 35 engaging the 9° sloping wall 44 of collet holder 40. The slightly greater angle of wall 35 of collet 30 relative to that of wall 44 of collet holder opening 41 results in the application of a transversely directed spring-like compressive force against collet 30 upon activation of locking ram 50 which firmly locks the needle in place.

When locking ram 50 is lowered, i.e., returned to the unlocked position, release of the compressive force against collet 30 results in rearward movement of the collet within collet holder 40 accompanied by a rearward ejection of the needle, now possessing a circumferential suture-cutting edge, from the collet bore.

In the embodiment shown, positional needle tolerance in the locked condition of the apparatus is held to a maximum deviation from the longitudinal axis of the needle of not more than about 0.00025°. Thus, the apparatus of this invention makes it possible to obtain very accurate positioning of the blunt end of the needle relative to the drill and to maintain this position throughout the socket and circumferential suture-cutting edge-forming operations. In the enlargement of the tip of drill 21 shown in FIG. 3B, the included angle formed by the sloping surfaces of the drill is established so as to define the value of inclusive angle x of the slope of the socket edge. In the embodiment shown, this angle is set at 100°.

During the cutting edge forming operation minute metal shavings or particles may tend to lodge within the socket. Prior to inserting the suture within the socket, it is preferred to remove these shavings employing any effective technique, for example, an ultrasonic cleaning operation.

The surgical needle of this invention is suitably combined with any of the various kinds of sutures known in the art. Such sutures are provided as monofilaments or braided structures and are manufactured from a variety of natural and synthetic materials including surgical gut, polyethylene, polypropylene, polyamide, polyethylene terephthalate, polyglycolic acid, glycolide-lactide copolymer, etc. Preferably, the suture is one of braided construction fabricated from a bio-absorbable or biodegradable resin such as one derived from polyglycolic acid, glycolide, lactic acid, lactide, dioxanone, trimethylene carbonate, etc., and various combinations of these and related monomers. Sutures prepared from resins of this type are known in the art, e.g., as disclosed in U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,137,921; 4,157,437; 4,234,775; 4,237,920; 4,300,565; and, 4,523,591; U.K. Patent No. 779,291; D. K. Gilding et al., "Biodegradable polymers for use in surgery—polyglycolic/poly(lactic acid) homo- and co-polymers: 1, Polymer, volume 20, pages 1459–1464 (1979), and D. F. Williams (ed.), *Biocompatibility of Clinical Implant Materials*, Vol. II, ch. 9: "Biodegradable Polymers" (1981).

Attachment of the suture to the surgical needle is generally accomplished by inserting one end of the suture into the socket formed within the blunt end of the needle. Crimping of the socket is sufficient to permanently secure the suture within the socket. For further additional details of techniques for attaching sutures to surgical needles of the socketed variety, reference may be made to the disclosure of U.S. Pat. No. 3,736,646, the contents of which are incorporated by reference herein.

What is claimed is:

1. In a combined surgical needle-suture which includes a surgical needle having a sharp end and a blunt end with a suture-receiving socket at said blunt end, a suture having one tip received within said socket and means for retaining the tip of the suture within the socket, the improvement which comprises a circumferential inwardly sloping surface defining the entrance to the socket, said sloping surface terminating at one end in the socket and at the other end in a circumferential cutting edge separated a distance from the suture, the slope of said being defined by an inclusive angle X the value of which is from about 90° to about 110°.

2. The surgical needle-suture combination of claim 1 wherein inclusive angle X is from about 95° to about 105°.

3. The surgical needle combination of claim 1 wherein the needle is fabricated from stainless steel.

4. A method for separating the suture component from the surgical needle component of a combined surgical needle-suture device wherein a tip of the suture is retained within a socket formed within the blunt end of the needle, said socket possessing a circumferential sloped entrance, which comprises:

(a) orienting the suture relative to the needle such that the suture is made to bear under a tensioning force against any location along a circumferential cutting edge separated a distance from the suture and formed upon the inwardly sloped entrance to the needle socket, said sloped surface being defined by an inclusive angle X the value of which is from about 90° to about 110°.

5. The method of claim 4 wherein the applied tensioning force is from about 3 ounces to about 4 pounds.

6. The method of claim 4 wherein the sloped surface of the socket possesses an inclusive angle X of from about 95° to about 105°.

7. The method of claim 6 wherein the applied tensioning of force is from about 6 ounces to about 2.5 pounds.

* * * * *